(12) United States Patent
Kim

(10) Patent No.: US 9,968,560 B2
(45) Date of Patent: May 15, 2018

(54) COMPOSITION FOR PREPARING SOFT CAPSULE SHELL

(71) Applicant: Mun Gu Kim, Seoul (KR)

(72) Inventor: Mun Gu Kim, Seoul (KR)

(73) Assignee: MUN GU KIM (KR)

( * ) Notice: Subject to any disclaimer, the term of this patent is extended or adjusted under 35 U.S.C. 154(b) by 0 days. days.

(21) Appl. No.: 15/363,227

(22) Filed: Nov. 29, 2016

(65) Prior Publication Data

US 2017/0172931 A1      Jun. 22, 2017

(30) Foreign Application Priority Data

Dec. 18, 2015 (KR) .......................... 10-2015-0181458

(51) Int. Cl.
    *A61K 9/48*       (2006.01)
(52) U.S. Cl.
    CPC ................................. *A61K 9/4816* (2013.01)
(58) Field of Classification Search
    CPC ...................................... A61K 9/4816
    See application file for complete search history.

(56) References Cited

U.S. PATENT DOCUMENTS 6,375,981 B1 * 4/2002 Gilleland ............. A61K 9/4816
                                                        424/451
2016/0136101 A1 * 5/2016 Sydow ................ A61K 9/4833
                                                        424/452

FOREIGN PATENT DOCUMENTS

| KR | 1020120128602 | 11/2012 | |
|----|---------------|---------|---|
| KR | 101212320 | 12/2012 | |
| KR | 101212320 B1 * | 12/2012 | ............... A61K 9/48 |

OTHER PUBLICATIONS

English machine translation of KR-101212320-B1 made Sep. 12, 2017. (Year: 2017).*

* cited by examiner

*Primary Examiner* — Michael B. Pallay
(74) *Attorney, Agent, or Firm* — Cantor Colburn LLP

(57) ABSTRACT

Provided is a composition for preparing a soft capsule shell that includes a non-animal material, and more particularly a composition for preparing a soft capsule shell, which includes modified starch composed of modified waxy corn starch and modified waxy potato starch, thereby realizing a soft capsule shell having appropriate hardness and elastic strength and delaying a browning phenomenon. The composition includes modified starch composed of modified waxy corn starch and modified waxy potato starch at a weight ratio of 2:8 to 8:2, a modified starch hydrolysate, a gelling agent, a plasticizer and purified water.

5 Claims, No Drawings

COMPOSITION FOR PREPARING SOFT CAPSULE SHELL

BACKGROUND OF THE INVENTION

1. Technical Field

The present invention relates to a composition for preparing a soft capsule shell, which includes a non-animal material, and more particularly to a composition for preparing a soft capsule shell, which includes modified starch comprising modified waxy corn starch and modified waxy potato starch, thereby realizing a soft capsule shell having appropriate hardness and elastic strength and delaying a browning phenomenon.

2. Description of the Related Art

Capsules for use in medicines or food are classified into hard capsules and soft capsules depending on the composition of the capsule shell.

The properties of typical hard capsules are determined by gelatin, which is contained in an amount of about 95 to 99 wt % based on the total weight of the composition thereof, whereas soft capsules contain about 30 to 70 wt % of gelatin, with the remainder of additives for improving the properties thereof.

Gelatin typically useful in soft capsules is mostly prepared by processing cattle hide, cattle bone or pig skin.

When gelatin is dissolved in a predetermined amount of water, the resulting solution has thermoreversible properties depending on changes in temperature. This means that gelatin exists as a viscous liquid colloid (sol) at high temperatures and is converted into a semi-solid phase (gel) at low temperatures. Due to these properties, gelatin is generally utilized in soft capsules.

Recently, societal acceptance of animal materials has decreased because of increased awareness of unsanitary processing and disease afflicting cattle and swine, such as mad cow disease or foot-and-mouth disease, and thus, research into non-animal materials and vegetable materials is ongoing.

Also, gelatin is obtained through hydrolysis of collagen and is configured such that amino acids are linked via peptide bonds to thus form linear or complicated branch structures.

In the case of soft capsules made of gelatin having such features, an intermolecular network is formed due to the components contained in capsules, such as aldehyde, tannin, and limonene, thus retarding the disintegration thereof. If the components of capsules have high pH, the hardness of capsule shells is drastically increased, undesirably leading to breakage of the capsules. On the other hand, if the pH thereof is low, to a level of 1.2 or less, the capsule shells are hydrolyzed and the contents thereof may leak, which is undesirable.

Hence, the preparation of soft capsules using carbohydrates derived from natural materials, in lieu of animal protein gelatin, has been studied for decades.

For example, there have been developed techniques regarding compositions for shells of chewable soft capsules including vegetable oil, perfume oil and amber gelatin and using a predetermined amount of starch, but acid-treated and chemically treated components are mainly used, undesirably resulting in harm to the environment and decreasing the binding strength of the capsules.

A conventional technique pertaining to the composition for forming a soft capsule film is disclosed in Korean Patent Application Publication No. 10-2012-0128602.

SUMMARY OF THE INVENTION

Accordingly, the present invention has been made keeping in mind the problems encountered in the related art, and the present invention is intended to provide a composition for preparing a soft capsule shell, which includes a non-animal material or a vegetable material, in lieu of an animal material.

In addition, the present invention is intended to provide a composition for preparing a soft capsule shell, which includes heat-treated modified starch, the amount of which is increased, thus exhibiting more environmentally friendly properties.

In addition, the present invention is intended to provide a composition for preparing a soft capsule shell, which includes modified starch comprising modified waxy corn starch and modified waxy potato starch, thus increasing the elastic strength of capsules and delaying browning or aging.

In addition, the present invention is intended to provide a composition for preparing a soft capsule shell, which includes a gelling agent, the amount of which is decreased compared to conventional compositions for preparing soft capsule shells, thus reducing the cost of manufacturing a soft capsule shell.

An aspect of the present invention provides a composition for preparing a soft capsule shell, comprising: modified starch comprising modified waxy corn starch and modified waxy potato starch at a weight ratio of 2:8 to 8:2, a modified starch hydrolysate, a gelling agent, a plasticizer, and purified water.

Also, the modified starch may further comprise modified waxy tapioca starch.

In an embodiment, the modified waxy corn starch may be heat-treated modified starch, and each of the modified waxy potato starch and the modified waxy tapioca starch may, independently, be acid-treated modified starch or oxidized modified starch.

Here, the modified waxy corn starch may be heat-treated modified waxy corn starch obtained through heat treatment at a temperature ranging from 120° C. to 130° C. for a period of time ranging from 10 min to 100 min.

In an embodiment, the modified starch may be contained in an amount of 10 to 60 wt % based on the total weight of the composition.

In an embodiment, the modified starch hydrolysate may include at least one selected from among waxy corn dextrin, waxy potato dextrin, and waxy tapioca dextrin.

In an embodiment, the gelling agent may include at least one selected from among iota-carrageenan, kappa-carrageenan, lambda-carrageenan, guar gum, arabic gum, tragacanth gum, karaya gum, ghatti gum, locust bean gum, tara gum, konjac gum, alginate, agar, pullulan, pectin, gellan, mannan, and xanthan gum.

In an embodiment, the plasticizer may include at least one selected from among glycerin, glucose, sorbitol, oligosaccharide, and crystalline fructose.

Also, the composition for preparing a soft capsule shell may further comprise at least one buffer agent selected from among calcium lactate, potassium metaphosphate, and calcium oxide.

In an embodiment, the composition for preparing a soft capsule shell may include 10 to 60 parts by weight of the modified starch, 2 to 20 parts by weight of the modified starch hydrolysate, 3 to 20 parts by weight of the gelling agent, 3 to 30 parts by weight of the plasticizer, and 30 to 70 parts by weight of the purified water.

According to the present invention, a composition for preparing a soft capsule shell includes an increased amount of heat-treated modified starch, and is thus more environmentally friendly, and also, a decrease in binding strength in chemically treated modified starch can be solved.

Also, as modified starch, the use of modified waxy corn starch and modified waxy potato starch can increase the elastic strength of capsules and can delay browning or aging.

Also, a gelling agent is used in a small amount compared to conventional compositions for preparing soft capsule shells, thus reducing the cost of manufacturing a soft capsule shell.

DESCRIPTION OF SPECIFIC EMBODIMENTS

The advantages and features of the present invention and methods for achieving them will be made clear from the embodiments described below in detail taken in conjunction with the accompanying drawings. However, the present invention is not limited to the embodiments disclosed herein, but may be modified into different forms. These embodiments are provided to thoroughly explain the disclosure and to sufficiently transfer the spirit of the present invention to those skilled in the art, and the present invention is merely defined by the scope of the claims. Throughout the specification, the same reference numerals designate the same components.

Hereinafter, a detailed description will be given of a composition for preparing a soft capsule shell according to an embodiment of the present invention.

An aspect of the present invention addresses a composition for preparing a soft capsule shell, comprising modified starch comprising modified waxy corn starch and modified waxy potato starch at a weight ratio of 2:8 to 8:2.

Starch is contained in cereals, potatoes, sweet potatoes, cassava (tapioca) and the like, and may be classified into amylose, having a linear chain structure, and amylopectin, having a spiral chain structure, depending on the structure thereof.

Buckwheat, barley, sorghum, corn, wheat, potatoes, sweet potatoes and rice are typically composed of about 15 to 30% amylose and 70 to 85% amylopectin. Meanwhile, waxy corn, waxy potato and waxy tapioca are composed mainly of amylopectin.

Since waxy corn, waxy potato and waxy tapioca contain almost no amylose-based starch, they are transparent and are able to maintain viscosity at low temperatures.

Typically, modified starch is obtained via the chemical treatment of starch, and examples thereof may include acid-treated starch, enzyme-treated starch, oxidized starch, crosslinked starch, and other starch derivatives.

Due to interactions between various functional groups present in the starch structure obtained through chemical treatment, the hardness of a soft capsule may be excessively increased, undesirably leading to the breakage of the soft capsule or deteriorating the binding strength of the soft capsule shell.

Hence, the present invention is undertaken to propose a composition for preparing a soft capsule shell, which is made stable through the use of modified starch, some or all of which may include heat-treated modified starch.

For example, the modified starch may include a mixture comprising heat-treated modified waxy corn starch and acid-treated modified waxy potato starch or a mixture comprising heat-treated modified waxy corn starch and acid-treated modified waxy potato starch or oxidized modified waxy potato starch.

Also, the modified starch may further include modified waxy tapioca starch.

As such, the modified waxy corn starch may be heat-treated modified starch, and each of the modified waxy potato starch and the modified waxy tapioca starch may, independently, be acid-treated starch or oxidized modified starch.

Examples of the modified starch may include a mixture comprising heat-treated modified waxy corn starch, acid-treated modified waxy potato starch and acid-treated modified waxy tapioca starch, or a mixture comprising heat-treated modified waxy corn starch, acid-treated modified waxy potato starch and acid-treated modified waxy tapioca starch.

The heat-treated modified starch may be prepared through heat treatment at a temperature ranging from 120° C. to 130° C. for a period of time ranging from 10 min to 100 min.

In the preparation of the heat-treated modified waxy corn starch, the internal pressure of a vessel is reduced and pressurized vapor is applied so that the internal temperature of the vessel is set to 120 to 130° C. before heat treatment. Thereafter, reducing the pressure is further performed and then pressurized vapor is applied again.

If the heat treatment is performed at a temperature lower than 100° C., there is no processing effect. On the other hand, if the heat treatment is performed at a temperature higher than 130° C., the structure of the starch may break down, leading to the concern of decreased absorption in the body.

When the starch is subjected to heat treatment within the above temperature range, the resulting heat-treated modified starch may have low viscosity and low tendency to denature during storage at a low temperature for a long period of time.

The heat-treated modified starch obtained through heat treatment under reduced pressure exhibits low tendency to denature due to low hygroscopicity when mixed with other materials, and may also delay the aging of materials.

Furthermore, the modified starch may contain 1% or less, and preferably 0.5% or less, of at least one substituent selected from among a carboxyl group, an acetyl group, an adipic acid group, vinyl acetate, propylene chlorohydrin, a hydroxypropyl group, and a phosphate.

In an embodiment of the present invention, the modified starch may be contained in an amount of 10 to 60 wt % based on the total weight of the composition for preparing a soft capsule shell.

Particularly, when a mixture comprising heat-treated modified starch and chemically treated modified starch is used, the amount of the heat-treated modified starch may be at least 20 wt % based on the total weight of the modified starch.

If the amount of the heat-treated modified starch is less than 20 wt % based on the total weight of the modified starch, the relative amount of chemically treated starch may be excessively increased, and thus the hardness of a soft capsule may become remarkably high, undesirably leading to the breakage of the soft capsule or deteriorating the binding strength of the soft capsule shell.

Based on the total weight of the modified starch, the amount of heat-treated modified starch may be 80 wt % or less. If the amount of the heat-treated modified starch exceeds 80 wt % based on the total weight of the modified starch, the hardness of a soft capsule may decrease.

In an embodiment of the present invention, the use of the heat-treated modified starch may reduce the amount of the chemically treated starch, thereby increasing the elastic strength of the manufactured soft capsule.

Furthermore, according to the present invention, a mixture comprising modified waxy corn starch and modified waxy potato starch is used. As such, the modified waxy corn starch and the modified waxy potato starch may be mixed at a weight ratio of 2:8 to 8:2.

Here, the modified waxy potato starch may be heat-treated modified starch or chemically treated modified starch, and is more viscous than the modified waxy corn starch, thus increasing the hardness of a soft capsule.

If the amount of the modified waxy potato starch is much higher than the amount of the modified waxy corn starch (e.g. if the modified waxy corn starch and the modified waxy potato starch are mixed at a ratio of 1:9), the viscosity of the composition becomes too high, making it difficult to perform the manufacturing process, and also, the hardness of a soft capsule becomes too high, undesirably leading to the breakage of the soft capsule or deteriorating the binding strength of the soft capsule shell.

On the other hand, if the amount of the modified waxy potato starch is much lower than that of the modified waxy corn starch (e.g. if the modified waxy corn starch and the modified waxy potato starch are mixed at a ratio of 9:1), it is difficult to obtain a soft capsule having sufficient hardness.

When the modified waxy corn starch and the modified waxy potato starch are used within the above amount range, appropriate hardness and high elastic strength of a capsule may be ensured and browning or aging may be delayed.

Furthermore, in the present invention, the use of the modified waxy potato starch may advantageously reduce the cost of manufacturing a soft capsule shell by decreasing the amount of the gelling agent compared to conventional compositions for preparing soft capsule shells.

Since the modified waxy potato starch has high viscosity, even when the amount of the gelling agent of the invention is lower than that of a gelling agent contained in a conventional composition for preparing a soft capsule shell, it is possible to manufacture a soft capsule having appropriate hardness and elastic strength.

Also, the composition of the present invention may further include a modified starch hydrolysate, a gelling agent, a plasticizer and purified water.

The modified starch hydrolysate may be at least one selected from among waxy corn dextrin, waxy potato dextrin, and waxy tapioca dextrin.

The composition for use in manufacturing a soft capsule includes a combination of the modified starch and the modified starch hydrolysate, thereby further increasing the transparency of a soft capsule.

In order to enhance the binding strength between modified starch components or between modified starch and other materials, the gelling agent may be used, and may include at least one selected from among iota-carrageenan, kappa-carrageenan, lambda-carrageenan, guar gum, arabic gum, tragacanth gum, karaya gum, ghatti gum, locust bean gum, tara gum, konjac gum, alginate, agar, pullulan, pectin, gellan, mannan, and xanthan gum.

Specifically, arabic gum is effectively utilized as a binder, xanthan gum may function to improve the tension of a capsule shell, that is, the extent of contraction and relaxation, and locust bean gum plays a role in supplementing strength to inhibit the breakage of the shell.

Also, gellan gum is used to improve the degree of disintegration of a soft capsule, and guar gum is effective at decreasing disintegration time and enhancing adhesion.

Also, iota-carrageenan, kappa-carrageenan, and lambda-carrageenan are good at preventing the release of water and maintaining hardness.

In particular, iota-carrageenan, kappa-carrageenan, and lambda-carrageenan may be prepared through a dehydration process.

Typically, carrageenan tends to deteriorate the binding strength between starch and other materials in a gelling process due to the potential presence of residual methyl alcohol and isopropyl alcohol (in amounts of less than 0.1% when used alone or in combination with each other based on FAO), which are used to recover carrageenan during the manufacturing process.

With the goal of solving the above problem, used in the present invention are iota-carrageenan, kappa-carrageenan, and lambda-carrageenan, which are prepared using a dehydration process, in place of a conventional alcohol precipitation process using an alcohol such as methyl alcohol or isopropylene alcohol.

Also, the composition of the present invention may include the plasticizer. Here, the plasticizer may be at least one selected from among glycerin, glucose, sorbitol, oligosaccharide, and crystalline fructose.

Specifically, the composition for preparing a soft capsule shell may comprise 10 to 60 parts by weight of the modified starch, 2 to 20 parts by weight of the modified starch hydrolysate, 3 to 20 parts by weight of the gelling agent, 3 to 30 parts by weight of the plasticizer and 30 to 70 parts by weight of the purified water.

If the amount of the modified starch is less than 10 parts by weight, there is a concern about decreased hardness of a soft capsule. On the other hand, if the amount thereof exceeds 60 parts by weight, the hardness of the soft capsule is excessively increased, undesirably deteriorating the binding strength of the soft capsule.

When the modified starch hydrolysate is contained within the above amount range, the transparency of a soft capsule shell and the ability to form a film may be increased.

If the amount of the gelling agent is less than 3 parts by weight, binding between modified starch components or between modified starch and other materials may become insufficient, and thus the hardness and elastic strength of the soft capsule shell may decrease. On the other hand, if the amount of the gelling agent exceeds 20 parts by weight, the fluidity of the composition for preparing a soft capsule shell may drastically decrease, making it very difficult to perform the manufacturing process and breaking the soft capsule due to the excessively high hardness of the soft capsule shell.

If the amount of the plasticizer is less than 3 parts by weight, the materials may be insufficiently mixed, or the solubility of the materials may decrease. On the other hand, if the amount of the plasticizer exceeds 30 parts by weight, the hardness and elastic strength of the soft capsule shell may decrease.

The composition for preparing a soft capsule shell according to the present invention may further include a buffer agent, thereby increasing the solubility of modified starch and increasing the binding strength of the capsule shell.

The buffer agent may be at least one selected from among calcium lactate, potassium metaphosphate and calcium oxide. For example, the amount thereof may be set to 2 wt % or less based on the total weight of the composition for preparing a soft capsule shell.

Also, the composition for preparing a soft capsule shell according to the present invention may further include a colorant, a fragrance, and/or a preservative.

A better understanding of the present invention is given through the following examples, which are merely set forth to illustrate but are not construed to limit the present invention.

Preparation of Composition for Preparing Soft Capsule Shell and Manufacture of Soft Capsule In order to evaluate the physical properties of a soft capsule shell manufactured using a composition for preparing a soft capsule shell, the compositions of Examples and Comparative Examples were prepared as shown in Tables 1 to 4 below.

Each of the compositions shown in Tables 1 to 4 was dissolved in a 90° water bath for 30 min and allowed to stand for 2 hr to remove foam therefrom, thus obtaining a composition for preparing a soft capsule shell.

Subsequently, each composition was processed in the form of a sheet, which was then filled with contents using a die roll, thus manufacturing a soft capsule.

TABLE 1

|  | Material | C. Ex. 1 | C. Ex. 2 | Ex. 1 |
|---|---|---|---|---|
| Modified starch | Heat-treated modified waxy corn starch | — | — | 25 |
|  | Acid-treated modified waxy potato starch | — | 20 | 5 |
|  | Acid-treated modified waxy tapioca starch | — | 10 | — |
|  | Oxidized modified tapioca starch | 22 | — | — |
|  | Oxidized modified potato starch | 8 | — | — |
| Starch hydrolysate | Heat-treated waxy corn dextrin | 3 | 3 | 3 |
|  | Waxy potato dextrin | 2 | 2 | 2 |
|  | Waxy tapioca dextrin | 2 | 2 | 2 |
|  | Waxy corn dextrin | 2 | 2 | 2 |
| Gelling agent | Iota-carrageenan | 4 | 4 | 4 |
|  | Kappa-carrageenan | 0.95 | 0.95 | 0.95 |
|  | Lambda-carrageenan | 2 | 2 | 2 |
| Plasticizer | Sorbitol | 1 | 1 | 1 |
|  | Glycerin | 13 | 13 | 13 |
| Purified water |  | 40 | 40 | 40 |
| Buffer agent | Calcium lactate | 0.01 | 0.01 | 0.01 |
|  | Potassium metaphosphate | 0.02 | 0.02 | 0.02 |
|  | Calcium oxide | 0.02 | 0.02 | 0.02 |

(unit: wt %)

TABLE 2

|  | Material | C. Ex. 3 | C. Ex. 4 | Ex. 2 |
|---|---|---|---|---|
| Modified starch | Heat-treated modified waxy corn starch | 18 | 18 | 20 |
|  | Acid-treated modified waxy potato starch | — | — | 10 |
|  | Acid-treated modified waxy tapioca starch | — | — | — |
|  | Oxidized modified tapioca starch | — | 12 | — |
|  | Oxidized modified potato starch | 12 | — | — |
| Starch hydrolysate | Heat-treated waxy corn dextrin | 3 | 3 | 3 |
|  | Waxy potato dextrin | 2 | 2 | 2 |
|  | Waxy tapioca dextrin | 2 | 2 | 2 |
|  | Waxy corn dextrin | 2 | 2 | 2 |
| Gelling agent | Iota-carrageenan | 4 | 4 | 4 |
|  | Kappa-carrageenan | 0.95 | 0.95 | 0.95 |
|  | Lambda-carrageenan | 2 | 2 | 2 |
| Plasticizer | Sorbitol | 1 | 1 | 1 |
|  | Glycerin | 13 | 13 | 13 |
| Purified water |  | 40 | 40 | 40 |
| Buffer agent | Calcium lactate | 0.01 | 0.01 | 0.01 |
|  | Potassium metaphosphate | 0.02 | 0.02 | 0.02 |
|  | Calcium oxide | 0.02 | 0.02 | 0.02 |

(unit: wt %)

TABLE 3

|  | Material | C. Ex. 5 | C. Ex. 6 | Ex. 3 |
|---|---|---|---|---|
| Modified starch | Heat-treated modified waxy corn starch | 3 | 27 | 15 |
|  | Acid-treated modified waxy potato starch | 27 | — | 15 |
|  | Acid-treated modified waxy tapioca starch | — | 3 | — |
|  | Oxidized modified tapioca starch | — | — | — |
|  | Oxidized modified potato starch | — | — | — |
| Starch hydrolysate | Heat-treated waxy corn dextrin | 3 | 3 | 3 |
|  | Waxy potato dextrin | 2 | 2 | 2 |
|  | Waxy tapioca dextrin | 2 | 2 | 2 |
|  | Waxy corn dextrin | 2 | 2 | 2 |
| Gelling agent | Iota-carrageenan | 4 | 4 | 4 |
|  | Kappa-carrageenan | 0.95 | 0.95 | 0.95 |
|  | Lambda-carrageenan | 2 | 2 | 2 |

TABLE 3-continued

| | Material | C. Ex. 5 | C. Ex. 6 | Ex. 3 |
|---|---|---|---|---|
| Plasticizer | Sorbitol | 1 | 1 | 1 |
| | Glycerin | 13 | 13 | 13 |
| Purified water | | 40 | 40 | 40 |
| Buffer agent | Calcium lactate | 0.01 | 0.01 | 0.01 |
| | Potassium metaphosphate | 0.02 | 0.02 | 0.02 |
| | Calcium oxide | 0.02 | 0.02 | 0.02 |

(unit: wt %)

TABLE 4

| | Material | C. Ex. 7 | Ex. 4 | Ex. 5 | Ex. 6 |
|---|---|---|---|---|---|
| Modified starch | Heat-treated modified waxy corn starch | — | 10 | 10 | 10 |
| | Acid-treated modified waxy potato starch | — | 23 | 10 | 10 |
| | Acid-treated modified waxy tapioca starch | — | — | 10 | 5 |
| | Oxidized modified tapioca starch | 10 | — | — | 5 |
| | Oxidized modified potato starch | 23 | — | — | — |
| Starch hydrolysate | Heat-treated waxy corn dextrin | 3 | 3 | 3 | 3 |
| | Waxy potato dextrin | 2 | 2 | 2 | 2 |
| | Waxy tapioca dextrin | 2 | 2 | 2 | 2 |
| | Waxy corn dextrin | 1 | 1 | 2 | 2 |
| Gelling agent | Iota-carrageenan | 3 | 3 | 4 | 3 |
| | Kappa-carrageenan | 0.95 | 0.95 | 0.95 | 0.95 |
| | Lambda-carrageenan | 1 | 1 | 2 | 3 |
| Plasticizer | Sorbitol | 1 | 1 | 1 | 1 |
| | Glycerin | 13 | 13 | 13 | 13 |
| Purified water | | 40 | 40 | 40 | 40 |
| Buffer agent | Calcium lactate | 0.01 | 0.01 | 0.01 | 0.01 |
| | Potassium metaphosphate | 0.02 | 0.02 | 0.02 | 0.02 |
| | Calcium oxide | 0.02 | 0.02 | 0.02 | 0.02 |

(unit: wt %)

Evaluation of Physical Properties of Soft Capsules

The soft capsules manufactured as above were dried for 10 hr, and then measured for disintegration start time, disintegration end time, hardness, elastic strength and film oxygen permeability.

(1) Disintegration Start Time and Disintegration End Time

The dried soft capsules were placed in a DR-8-type dissolution tester and then subjected to hot-water heating at 37° C., after which the disintegration start time, at which the disintegration of the soft capsules was initiated, and the disintegration end time, at which the complete disintegration of the soft capsules was realized, were measured.

The results of measurement of disintegration start time and disintegration end time are shown in Table 5 below.

TABLE 5

| No. | Disintegration start time | Disintegration end time |
|---|---|---|
| Ex. 1 | 3 min 30 sec | 12 min 30 sec |
| Ex. 2 | 3 min 40 sec | 13 min 10 sec |
| Ex. 3 | 3 min 40 sec | 12 min 20 sec |
| Ex. 4 | 3 min 30 sec | 12 min 00 sec |
| Ex. 5 | 3 min 30 sec | 12 min 10 sec |
| Ex. 6 | 3 min 40 sec | 12 min 30 sec |
| C. Ex. 1 | 3 min 50 sec | 13 min 30 sec |
| C. Ex. 2 | 4 min 30 sec | 14 min 20 sec |
| C. Ex. 3 | 4 min 10 sec | 14 min 30 sec |
| C. Ex. 4 | 4 min 30 sec | 14 min 10 sec |
| C. Ex. 5 | 4 min 40 sec | 13 min 50 sec |
| C. Ex. 6 | 4 min 10 sec | 14 min 30 sec |
| C. Ex. 7 | 4 min 30 sec | 13 min 40 sec |

As is apparent from Table 5, the disintegration start time and the disintegration end time of Examples 1 to 6 were shorter than those of Comparative Examples 1 to 7.

The combination of heat-treated modified waxy corn starch and modified waxy potato starch can be found to alleviate the delayed disintegration problem.

(2) Measurement of Hardness and Elastic Strength 6 soft capsules manufactured using the composition of each of Examples 1 to 6 and Comparative Examples 1 to 6 were allowed to stand at 20° C. for 12 hr, after which the hardness thereof was measured using a FUDOH Rheometer with a plunger having an area of 1.0 cm$^2$.

The elastic strength was determined by applying a load at a speed of 10 mm/min using a 250 N fatigue tester (E1000, available from INSTRON) under conditions of 24.2±2.0° C. and 49±10% relative humidity (R.H.) and measuring the maximum compressive load (elastic strength: N).

The results of measurement of hardness and elastic strength are shown in Table 6 below.

TABLE 6

| No. | Hardness (g/cm$^2$) | Elastic strength (N) |
|---|---|---|
| Ex. 1 | 3750 | 90 |
| Ex. 2 | 3980 | 94 |
| Ex. 3 | 4050 | 92 |
| Ex. 4 | 4210 | 108 |
| Ex. 5 | 4050 | 104 |
| Ex. 6 | 3980 | 98 |
| C. Ex. 1 | 3950 | 82 |
| C. Ex. 2 | 4240 | 86 |
| C. Ex. 3 | 3780 | 79 |
| C. Ex. 4 | 3650 | 72 |
| C. Ex. 5 | 4580 | 85 |
| C. Ex. 6 | 4030 | 87 |
| C. Ex. 7 | 3650 | 72 |

As is apparent from Table 6, the soft capsules of Examples 1 to 6 had appropriate hardness, thereby preventing the soft capsules from breaking or the binding strength thereof from decreasing. Furthermore, the soft capsules of the invention exhibited superior elastic strength to thus increase storage stability, compared to conventional soft capsules.

(3) Measurement of Film Oxygen Permeability

According to the ASTM F 1927:2014 method at 23±1° C., the film oxygen permeability of the manufactured soft capsules was measured based on a capsule shell standard corresponding to a thickness of 0.28 mm using an OX-TRAN, Model 2/61 (MOCON, USA) as an oxygen permeability tester.

The results of measurement of film oxygen permeability are shown in Table 7 below.

TABLE 7

| No. | Film oxygen permeability ($cm^3/(m^2 \cdot day)$) |
|---|---|
| Ex. 1 | 0.8 |
| Ex. 2 | 0.8 |
| Ex. 3 | 0.9 |
| Ex. 4 | 0.7 |
| Ex. 5 | 0.8 |
| Ex. 6 | 0.9 |
| C. Ex. 1 | 1.2 |
| C. Ex. 2 | 1.3 |
| C. Ex. 3 | 1.4 |
| C. Ex. 4 | 1.8 |
| C. Ex. 5 | 2.4 |
| C. Ex. 6 | 1.2 |
| C. Ex. 7 | 1.5 |

As the film oxygen permeability decreases, the film structure can be found to be very compact. In the soft capsules of Examples 1 to 6, the shells are found to be quite dense compared to the soft capsules of Comparative Examples 1 to 7.

Although the preferred examples and test examples of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A composition for preparing a soft capsule shell, comprising:
   modified starch, comprising acid-treated modified waxy potato starch;
   a modified starch hydrolysate, comprising at least one selected from among waxy corn dextrin, waxy potato dextrin and waxy tapioca dextrin;
   a gelling agent;
   a plasticizer; and
   purified water,
   wherein a soft capsule shell prepared using the composition has a film oxygen permeability of 1.0 $cm^3/(m^2 \cdot day)$ or less.

2. The composition of claim 1, wherein the modified starch further comprises modified waxy tapioca starch, and the modified waxy tapioca starch is contained in an amount identical to an amount of the modified waxy potato starch.

3. The composition of claim 2, wherein the modified waxy tapioca starch is acid-treated modified starch or oxidized modified starch.

4. The composition of claim 1, wherein the modified starch is contained in an amount of 10 to 60 wt % based on a total weight of the composition.

5. The composition of claim 1, wherein the composition comprises:
   10 to 60 parts by weight of the modified starch;
   2 to 20 parts by weight of the modified starch hydrolysate;
   3 to 20 parts by weight of the gelling agent;
   3 to 30 parts by weight of the plasticizer; and
   30 to 70 parts by weight of the purified water.

* * * * *